US00PP37367P3

(12) United States Plant Patent
Olesen

(10) Patent No.: US PP37,367 P3
(45) Date of Patent: Apr. 14, 2026

(54) HYBRID TEA ROSE PLANT NAMED 'Poulpmt010'

(50) Latin Name: *Rosa hybrida*
Varietal Denomination: Poulpmt010

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/831,797

(22) Filed: Sep. 15, 2025

(65) Prior Publication Data

US 2026/0083036 P1 Mar. 19, 2026

(30) Foreign Application Priority Data

Sep. 19, 2024 (QZ) ..... PBR 20242182

(51) Int. Cl.
*A01H 5/02* (2018.01)
*A01H 6/74* (2018.01)

(52) U.S. Cl.
USPC ..... Plt./131
CPC ..... *A01H 6/749* (2018.05); *A01H 5/02* (2013.01)

(58) Field of Classification Search
USPC ..... Plt./101, 130, 133, 1
See application file for complete search history.

(56) References Cited

U.S. PATENT DOCUMENTS

PP35,384 P2 * 9/2023 Bedard ..... A01H 6/749 Plt./131

* cited by examiner

*Primary Examiner* — Susan McCormick Ewoldt

(57) ABSTRACT

A new garden rose plant of the Hybrid Tea class which has abundant, red and orange yellow reverse bi-color flowers and attractive foliage. This now and distinct variety has shown to be uniform and stable in the resulting generations from asexual propagation.

2 Drawing Sheets

Botanical designation: *Rosa hybrida.*

Variety denomination: 'Poulpmt010'.

This application claims priority to Plant Breeder's Rights Application Number 2024/2182, which was filed at the Community Plant Variety Rights Office in the European Union on Sep. 19, 2024, the contents of which are hereby incorporated by reference for all purposes.

SUMMARY OF THE INVENTION

The present invention constitutes a new and distinct variety of hybrid tea rose plant which originated from a controlled crossing between the female seed parent, an unnamed seedling, and the male pollen parent, also an unnamed seedling. Both of the parent varieties are non-patented.

The two parents were crossed during the summer of 2012 and the resulting seeds were planted in a controlled environment in Odense, Denmark. The new variety, named 'Poulpmt010', originated as a single seedling from the stated cross.

The new variety may be distinguished from its male pollen parent and female seed parent primarily by the following characteristics. The male pollen parent plant has light pink flowers while the new variety has red and orange yellow reverse bi-color flowers. Flowers of the female seed parent plant exhibit colours of Red-Purple Group N57A and Yellow Group 12A, while colours exhibited in 'Poulmpt010' are primarily Red Group 53C and Orange Group 27A.

The objective of the hybridization of this rose variety was to create a new and distinct variety with unique qualities, such as:

1. Uniform and abundant red and orange yellow reverse bi-color flowers;
2. Strong rose perfumed scent,
3. Vigorous, but compact growth when propagated on its own roots; and
4. Exceptional disease resistance.

This combination of qualities is not present in previously available commercial cultivars of this type, known to the inventor, and distinguish 'Poulpmt010' from all other varieties of which we are aware.

As part of the rose development program, Mogens N. Olesen germinated the seeds from the aforementioned hybridization during winter of 2012 and conducted evaluations on the resulting seedlings in a controlled environment in Odense, Denmark. 'Poulpmt010' was selected in the spring of 2013 by the inventor as a single plant from the progeny of the aforementioned hybridization.

Asexual reproduction of 'Poulpmt010' by rooted cuttings was first done by Mogens N. Olesen in the nursery in Odense, Denmark in July 2013. This initial and other subsequent asexual propagations conducted in controlled environments have demonstrated that the characteristics of 'Poulpmt010' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpmt010'.

Specifically illustrated in FIG. 1 of the drawings are open flowers viewed from the side and above, flower petals detached showing distinct bi-colouration, sepals detached revealing the reproductive flower parts, and flower buds.

Figure 1:
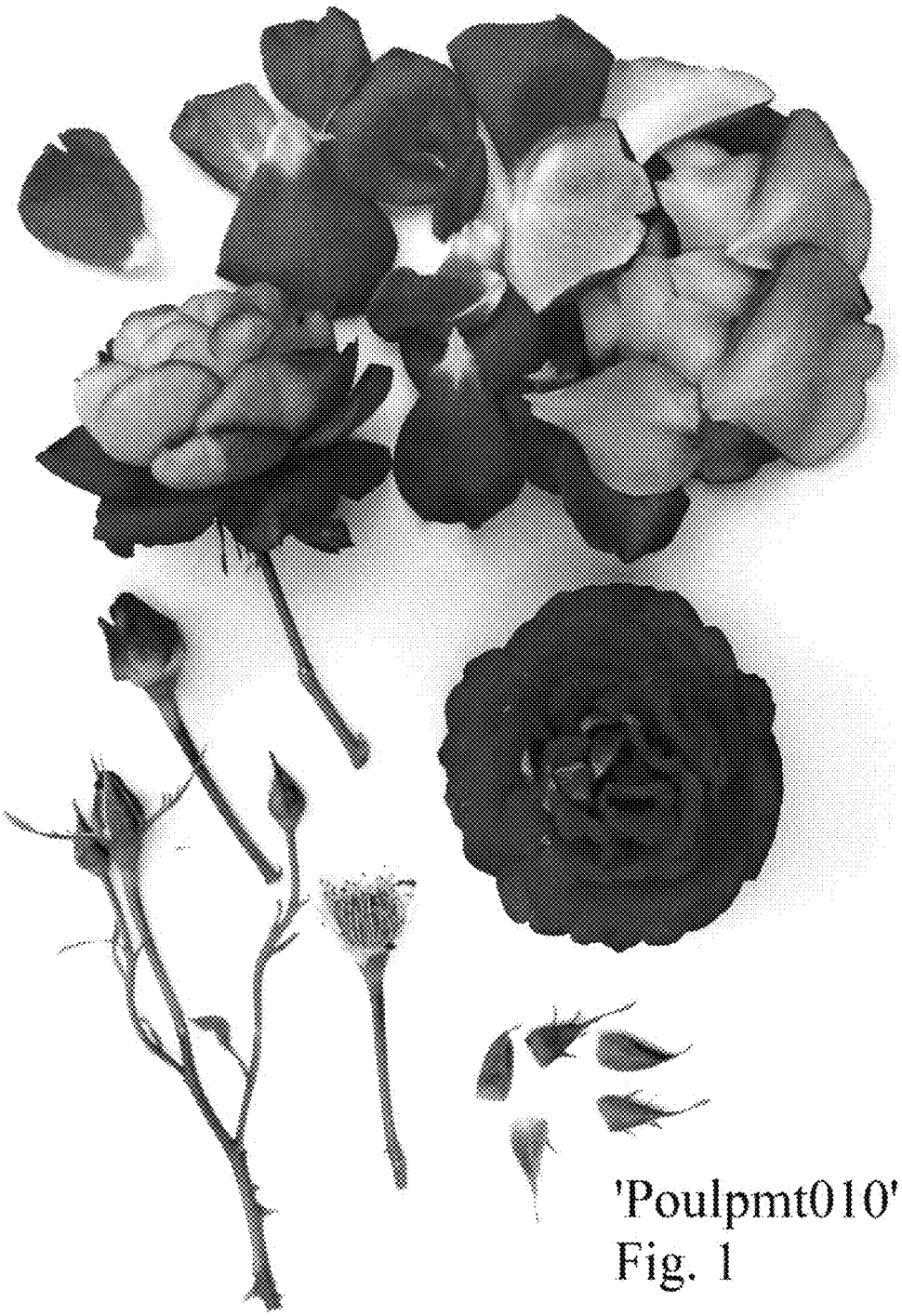
Figure 2:
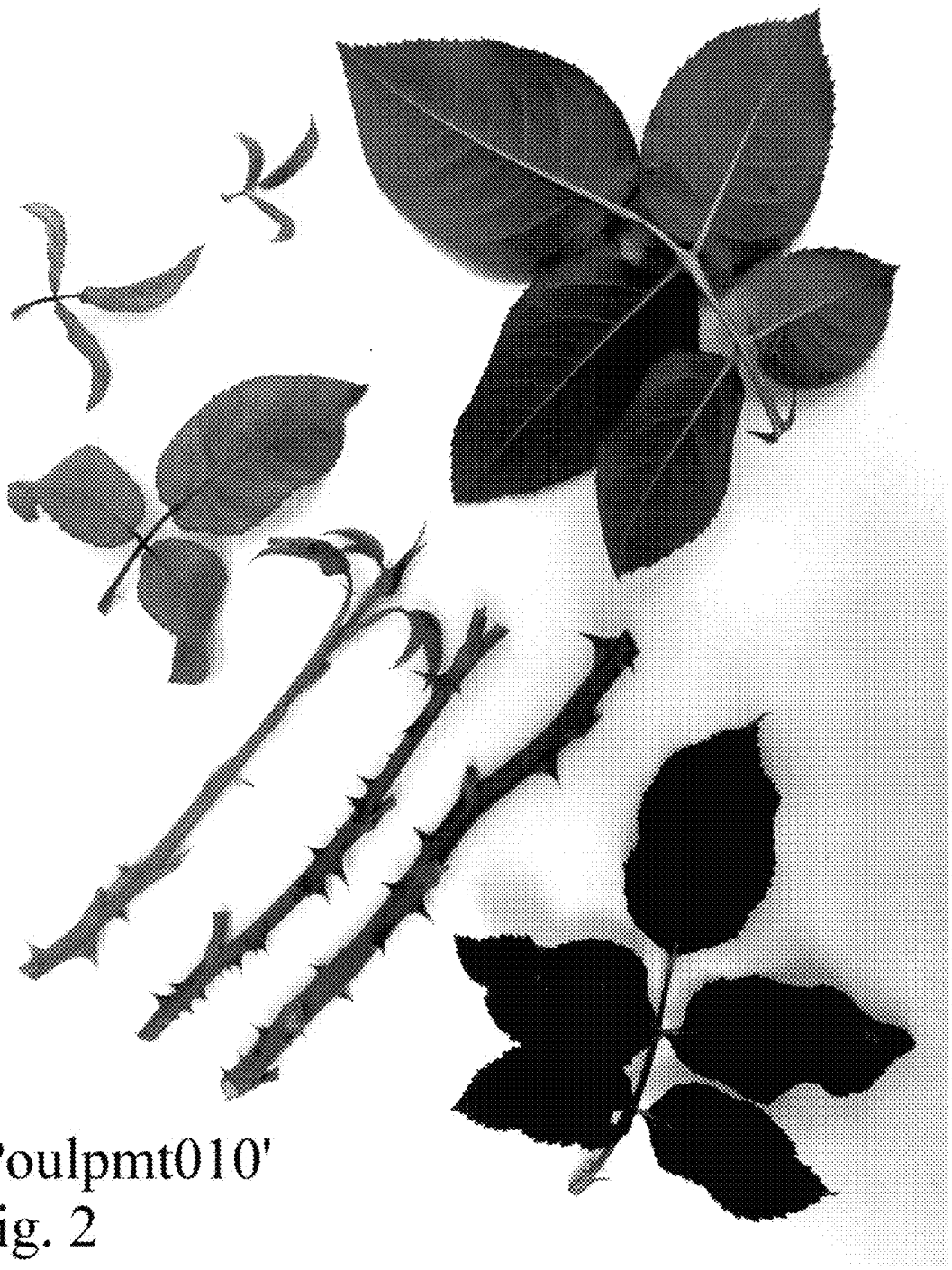

Specifically illustrated in FIG. 2 of the drawings are juvenile leaves, juvenile bare stem, mature leaves, and mature stem exhibiting prickles. Plants shown are 15 months of age.

DETAILED DESCRIPTION OF THE VARIETY

The following is a description of 'Poulpmt010', as observed in its growth in an outdoor nursery in Odense Denmark. Observed plants are 15 months of age, and were grown on their own roots in 30 cm pots. Color references are made using The Royal Horticultural Society (London, England) Colour Chart, 2001, except where common terms of color are used.

For a comparison, several physical characteristics of the most similar rose variety, 'WEKmamoprela', U.S. Plant Pat. No. 35,384, are compared to the claimed plant. While 'Poulpmt010' has 42 flower petals, 'WEKmamoprela' has 27 to 39 flower petals. The petal undersurface of 'Poulpmt010' is Orange Group 27A shaded with other intonations of Red Group 48D and Yellow Group 8B towards the basal zone. The upper petal surface of 'Poulmpt010' are Red Group 45B with intonations of Yellow Group 8A at the basal zone. The undersurface of flower petals of 'WEKmamoprela' are White 155D, & 155C, with other intonations of Red-Purple Group 64B at the margins. Above petal surface of 'WEKmamoprela' is Red-Purple Group 61C and 66B.

Flower and Flower Bud

Blooming habit: Continuous.

Flower bud:

*Size*.—Upon opening, about 30 mm in length from base of receptacle to end of bud. Bud diameter is 16 mm.

*Bud form*.—Ovoid.

*Bud color*.—As sepals divide petals are Yellow Group 2C and Red Group 47A.

*Sepal inner surface*.—Color: Yellow-Green Group 146D with intonations of Greyed-Purple Group 184B. Surface: Strong pubescent.

*Sepal outer surface*.—Color: Yellow-Green Group 144A with intonations of Greyed-Purple Group 183A. Texture: Smooth.

*Sepal shape*.—Apex: Cirrhose. Base: Flat at union with receptacle.

*Sepal margin*.—Margins have strong foliaceous appendages on three of the five sepals.

*Sepal size*.—About 39 mm long, 14 mm wide.

*Receptacle*.—Texture: Smooth. Size: 10 mm in height, 12 mm wide. Color: Yellow-Green Group 144A. Shape: Funnel.

*Pedicel*.—Surface: Smooth. Length: 30 to 65 mm. Diameter: 4 mm on average. Color: Yellow-Green Group 144A with intonations of Greyed-Purple Group 187B. Strength: Strong.

*Peduncle*.—Length: 3 to 5 cm. Diameter: About 4 mm. Color: Yellow-Green Group 144A with intonations of Greyed-Purple Group 183B. Texture: Smooth.

Flower bud development: Flower buds are borne single or in clusters of 3 to 5 flower buds per stem.

Flower bloom:

*Fragrance*.—Moderate to strong apple-like rose fragrance.

*Duration*.—The blooms have a duration on the plant of approximately 14 days. Petals fall cleanly away from plant after flowers have fully matured.

*Size*.—Flower diameter is about 110 mm when open. Flower depth is 60 mm.

*Flower shape*.—Open cup, double flower, with petals that curve out from the center.

*Shape of flower, side view*.—The upper portion is flat convex. The lower portion is flat.

Petalage: Under normal conditions, flowers have about 42 petals.

General tonality of flower: Open flowers are Red Group 53C and Orange Group 27A.

Petal color:

*Upon opening, outer petals*.—Upper surface: Red Group 45B with a large petal spot at the basal zone Yellow Group 8A. Lower surface: Orange Group 27A with shades of Red Group 48D. Other intonations at basal zone Yellow Group 8B.

*Upon opening, inner petals*.—Upper surface: Red Group 45B with a large petal spot at the basal zone Yellow Group 8A. Lower surface: Orange Group 29C. At basal zone shades of Yellow Group 8B. Marginal intonations are Red Group 50C.

*After opening, outer petals*.—Upper surface: Red-Purple Group N57A. Marginal intonations Red Group 53A. Basal zone Yellow Group 11B. Lower surface: Basal zone Yellow Group 11C. At the middle zone, Red Group 56B Marginal zone intonations of Red-Purple Group N57C.

*After opening, inner petals*.—Upper surface: Basal Yellow Group 8B. The middle and marginal zones are shaded with Red Group 53B. Lower surface: Basal Yellow Group 11C. Middle Orange Group 27A. Marginal zone Red Group 53D.

Petals:

*Petal reflex*.—None.

*Margin*.—Entire and uniform. Occasional cleft. Moderate undulations.

*Shape*.—Broad and elliptic. Apex shape: Rounded. Base shape: Acute.

*Size*.—75 mm (l)×70 mm (w).

*Texture*.—Soft.

*Thickness*.—Average.

Petaloids:

*Size*.—35 mm (l) by 20 mm (w).

*Quantity*.—About 8.

*Shape*.—Elliptical with an acute base and rounded apices.

*Color*.—Upper surface Yellow Group 8B at the basal zone and running in streaks. Middle and marginal zone Red Group 53B. Lower surface has a basal zone colour of Yellow Group 11C. The middle zone is Orange Group 27A. Marginal zone Red Group 53D.

Reproductive flower parts:

*Pollen*.—None observed.

*Anthers*.—Size: 1 mm in length. Color: Greyed-Orange Group 163B. Quantity: 60 on average.

*Filaments*.—Color: Yellow Group 12A with other intonations of Red Group 41B. Length: About 17 mm.

*Pistils*.—Length: 8 mm. Quantity: 48 on average.

*Stigmas*.—Color: Greyed-Yellow Group 160B.

*Styles*.—Color: Red Group 52A.

*Location of stigmas*.—Inferior in location relative to the length of the filaments and the height of the anthers.

*Hips*.—None Observed.

Plant

Plant growth: Upright. Plants are 80 to 90 cm in height, and 65 cm wide.

Stems:

*Color of juvenile growth*.—Yellow-Green Group 144A.

*Color of mature growth*.—Yellow-Green Group 146A.

*Length*.—Canes are about 55 cm from the base of the plant to the flowering portion.

*Diameter*.—About 8 mm.

*Internodes*.—On mature canes about 35 mm between nodes.

*Surface texture*.—Young wood: Smooth. Older wood: Smooth.

Long prickles:

*Incidence*.—About 15 prickles per 10 cm of stem.

*Size*.—Average length of prickles on mature stems is 8 mm.

*Shape*.—Upper portion is linear to concave. Lower portion is concave.

*Color*.—Juvenile prickles: Greyed-Red Group 179C. Mature prickles: Greyed-Red Group 181A.

Plant foliage:

*Compound leaf*.—190 mm (l)×200 (w).

*Quantity*.—2 leaves per 10 cm of stem on average.

*Leaf bearing angle to the stem*.—About 70 degrees.

*Color of juvenile foliage*.—Upper side: Yellow-Green Group N144A with intonations of Greyed-Orange Group 171A. Lower side: Yellow-Green Group 144B.

*Color of mature foliage*.—Upper side: Yellow-Green Group 147A. Lower side: Yellow-Green Group 146A.

Plant leaves and leaflets:

*Stipules*.—Size: 15 mm long, 3 mm wide. Quantity: 2 per compound leaf. Shape: Linear, slightly broad based with outward extending apices. Margins: Finely serrated. Color: Yellow-Green Group 144A.

*Petiole*.—Length: About 26 mm. Diameter: 2 to 3 mm. Upper surface color: Yellow-Green Group 144A. Lower surface color:

*Rachis*.—Length: About 55 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 105 mm long, 83 mm wide. Shape: Generally elliptical. Base: Rounded. Apex: Acute occasionally mucronate. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpmt010' substantially as described and illustrated herein.

* * * * *

'Poulpmt010'

'Poulpmt010'